US007427278B2

(12) United States Patent
Goudaliez et al.

(10) Patent No.: US 7,427,278 B2
(45) Date of Patent: Sep. 23, 2008

(54) EXTRACTION DEVICE WITH TUBES HAVING DIFFERENT CROSS-SECTIONS

(75) Inventors: Francis Goudaliez, Faches-Thumesnil (FR); Thierry Verpoort, Mouvaux (FR)

(73) Assignee: MacoPharma, Mouvaux (FR)

( * ) Notice: Subject to any disclaimer, the term of this patent is extended or adjusted under 35 U.S.C. 154(b) by 675 days.

(21) Appl. No.: 10/291,977

(22) Filed: Nov. 12, 2002

(65) Prior Publication Data

US 2003/0055396 A1 Mar. 20, 2003

Related U.S. Application Data

(63) Continuation of application No. PCT/FR01/01329, filed on Apr. 27, 2001.

(30) Foreign Application Priority Data

May 12, 2000 (FR) .................................. 00 06081

(51) Int. Cl.
*A61B 19/00* (2006.01)
(52) U.S. Cl. .................................................... 604/408
(58) Field of Classification Search ................ 604/408, 604/6.15, 6.16, 6.02, 403, 410, 416, 6.12, 604/131, 151, 246, 4.01, 411; 494/37; 73/863.21; 210/739, 782; 600/573
See application file for complete search history.

(56) References Cited

U.S. PATENT DOCUMENTS

| | | | | |
|---|---|---|---|---|
| 3,876,340 A | * | 4/1975 | Thomas | 417/475 |
| 4,086,924 A | * | 5/1978 | Latham, Jr. | 604/6.04 |
| 4,223,672 A | * | 9/1980 | Terman et al. | 604/6.06 |
| 4,385,630 A | * | 5/1983 | Gilcher et al. | 604/31 |
| 4,653,719 A | * | 3/1987 | Cabrera et al. | 251/7 |
| 4,886,431 A | * | 12/1989 | Soderquist et al. | 417/477.2 |
| 5,318,515 A | * | 6/1994 | Wilk | 604/30 |
| 5,380,173 A | * | 1/1995 | Hellstrom | 417/477.3 |
| 5,443,451 A | * | 8/1995 | Chapman et al. | 604/153 |
| 5,836,934 A | * | 11/1998 | Beshel | 604/410 |
| 5,853,382 A | * | 12/1998 | Kingsley et al. | 604/6.02 |
| 6,033,561 A | * | 3/2000 | Schoendorfer | 210/195.1 |
| 6,113,554 A | * | 9/2000 | Gilcher et al. | 600/573 |

FOREIGN PATENT DOCUMENTS

WO           01/85029         11/2001

OTHER PUBLICATIONS

International Search Report PCT/FR01/01329m, Mailed Jul. 18, 2001.

* cited by examiner

*Primary Examiner*—Nicholas D. Lucchesi
*Assistant Examiner*—Christopher D Koharski
(74) *Attorney, Agent, or Firm*—Baker Botts L.L.P.

(57) ABSTRACT

An extraction device for a biological fluid with an additive solution in which it is desirable for the additive solution to be present in a particular volume proportion to the biological fluid. The volume proportion of the additive solution is determined by the ratio of cross sections of two tubes, one which supplies the biological fluid to a collecting bag and a second which supplies the additive solution to a collecting bag. The tubes are periodically constricted in constriction areas by a pump. The tubes are configured so that the additive solution and the biological fluid only mix downstream of the constriction areas, thereby reducing the risk of supplying the additive solution to the source of the biological fluid. In an exemplary embodiment the biological fluid is blood collected from a patient or donor and the additive solution is an anticoagulant and/or preservation solution.

20 Claims, 2 Drawing Sheets

EXTRACTION DEVICE WITH TUBES HAVING DIFFERENT CROSS-SECTIONS

PRIORITY CLAIM

The present application is a continuation under 35 U.S.C. §120 of pending International Phase PCT application PCT/FR01/01329 filed on Apr. 27, 2001 designating the US and claiming priority to FR 00/06081 filed May 12, 2000, both applications incorporated by reference herein. PCT/FR01/01329 was published in French as WO 01/85029 on Nov. 15, 2001.

FIELD OF THE INVENTION

The invention relates to a device for extracting a biological fluid to which an anticoagulant and/or preservation solution is added.

BACKGROUND OF THE INVENTION

The present invention may be used when whole blood is taken from a donor for collection in a sterile fashion in a collecting bag.

To prevent coagulation of the blood in the collecting bag, it is conventional for the collecting bag to be filled prior to extracting with an additive anticoagulant and/or preservation solution.

One of the problems with such a system lies in producing a homogeneous mixture between the solution contained in the bag and the extracted blood. This is conventionally done by stirring the collecting bag.

Another problem posed is controlling the volume proportion of additive solution in the extracted fluid. This is important, in particular in the field of blood collection, because the quantity of anticoagulant and/or preservation solution present in a bag of blood is fixed at a certain proportion so that the blood can be used in the medical field.

To resolve these problems, devices including a bag containing the anticoagulant and/or preservation solution and an initially empty collecting bag have been proposed. In such devices, pumps having two rotors, one for supplying extracted biological fluid and the other for supplying solution, are used. The two rotors rotate at different tangential speeds slaved to one another so as to obtain the required volume proportion of biological fluid and additive solution.

These devices leave ample room for improvement in that they require the use of a special complex pump structure which complicates their use whilst increasing the extraction cost.

In addition, U.S. Pat. No. 4,223,672 discloses an apparatus for the extracorporeal treatment of blood, in which a receptacle containing an anticoagulant is connected to a first tube by way of a fourth tube. This connection is effected upstream of a peristaltic pump which is designed to supply a receptacle with blood by way of the first tube. This patent indicates that the ratio between the cross-sections of the first and fourth tubes is chosen so as to obtain the required mixture of anticoagulant in the blood.

In this type of apparatus, because the connection between anticoagulant and biological fluid is made upstream of the pump, the flow of anticoagulant solution is directed towards the patient. This design therefore has in particular the drawback of risk of injection of anticoagulant solution into the patient.

SUMMARY OF THE INVENTION

The invention therefore aims to remedy these or other drawbacks by providing an extraction device in which it is possible to control the volume proportion of solution added to the extracted fluid using a peristaltic pump with a conventional structure, while preventing any accidental injection of additive solution into the patient.

To this end, an embodiment of the invention provides a device for extracting a fluid, in particular blood. The device includes a removal component for removing the fluid, at least one bag containing an additive anticoagulant and/or preservation solution, and at least one collecting bag intended to receive the extracted fluid and the additive anticoagulant and/or preservation solution. The collecting bag is in fluid communication with the removal component by way of at least a first flexible tube and with the additive bag by way of at least a second flexible tube. The device also includes a peristaltic pump able to partially constrict respectively the first and second tubes in a constriction area. The rate of constriction of each tube is substantially identical. However, the ratio between the cross-section of the second tube through which the added solution passes and that of the first tube through which the extracted biological fluid passes is substantially equal to the proportion in volume of anticoagulant and/or preservation solution to be added to the extracted fluid. Accordingly, when the pump is actuated, the collecting bag is supplied with the extracted fluid and with the anticoagulant and/or preservation solution in the desired volume proportions. Additionally, the first and second tubes are arranged to allow mixing of the anticoagulant and/or preservation solution with the extracted fluid downstream of the constriction area.

In a more specific embodiment, the peristaltic pump is able to constrict the first and second tubes simultaneously so as to supply the collecting bag with the extracted fluid and with the anticoagulant and/or preservation solution simultaneously.

In another embodiment, a junction is provided downstream of the constriction area so as to connect the first and second tubes to a first end of a third tube whose second end is connected to an input port of the collecting bag. The peristaltic pump may then include a motor actuating a shaft on which two identical cylindrical rotors are mounted. The rotors each carry rollers able to constrict respectively the first and second tubes.

According to another embodiment, upstream of the constriction area the first and second tubes are associated in a sealed fashion in a third tube whose downstream end is connected to an input port of the collecting bag.

In a further more specific embodiment, downstream of the constriction area the first and second tubes end so that the collecting bag is supplied with extracted fluid and anticoagulant and/or preservation fluid by way of the tube connected to the input port.

According to another embodiment, upstream of the constriction area, the second tube is introduced in a sealed fashion inside the first tube.

In a further more specific embodiment, downstream of the constriction area, the second tube ends so that the collecting bag is supplied with extracted fluid and anticoagulant and/or preservation fluid by way of the first tube.

According to any of the sealed tube embodiments, the peristaltic pump includes a motor actuating a shaft on which a cylindrical rotor is mounted. The rotor carries rollers able to constrict the first and second tubes.

In a particular embodiment, the ratio between the cross-section of the second tube through which the additive solution passes and that of the first tube through which the extracted fluid passes is between 0.05 and 0.5, in particular 0.14.

BRIEF DESCRIPTION OF THE DRAWINGS

The following figures form part of the present specification and are included to further demonstrate certain aspects of the present invention. The invention may be better understood by reference to one or more of these drawings in combination with the detailed description of specific embodiments presented herein.

DETAILED DESCRIPTION OF THE INVENTION

Figure 1:
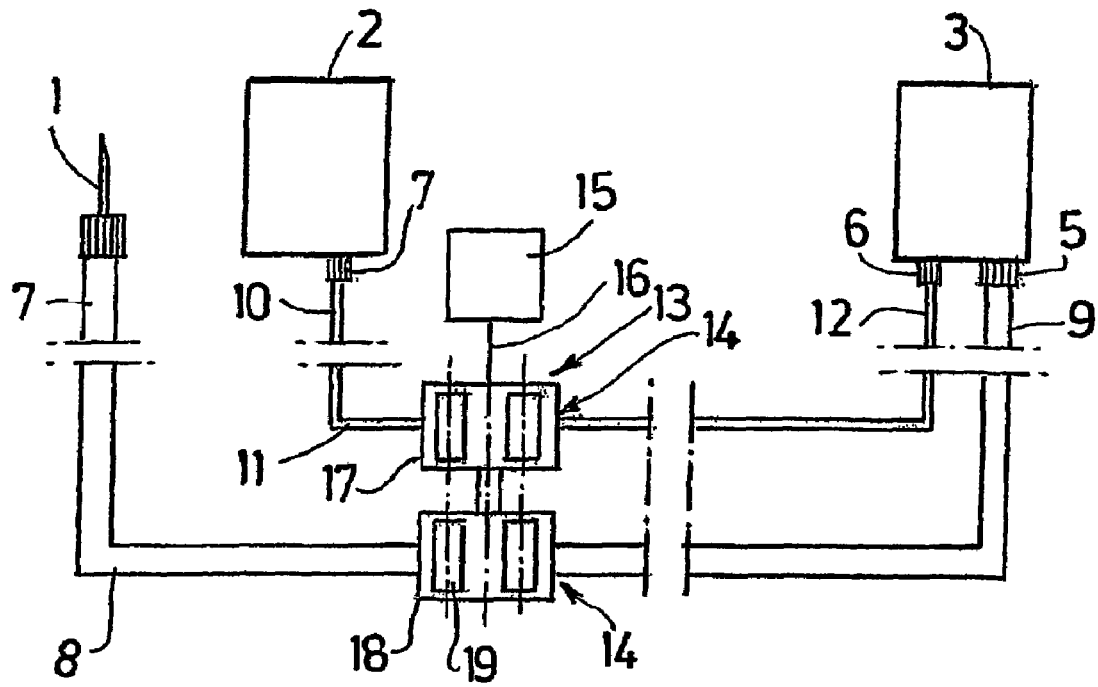
FIG. 1 depicts schematically, in elevation and flat views, a first variant of a first embodiment of an extraction device of the present invention in which the collecting bag is supplied directly by the first and second tubes, the tubes each being constricted by a different rotor.

Specific embodiments of the present invention and their advantages are best understood by reference to FIGS. 1 through 4, where like numbers are used to indicate like and corresponding features.

Throughout the present application, the terms "upstream" and "downstream" are defined respectively with respect to the direction of flow of the extracted fluid from the removal component 1 to the collecting bag 3.

In the particular embodiments depicted in the figures, a device for extracting a biological fluid comprises removal component 1 for removing the fluid, a bag 2 containing an additive anticoagulant and/or preservation solution for the extracted fluid and a collecting bag 3 intended to receive the extracted fluid to which the anticoagulant and/or preservation solution is added.

Such a device is in particular intended to collect the whole blood taken from a donor by way of removal component 1, for example formed by a needle. The anticoagulant and/or preservation solution is for example of the CPD type and is introduced into the bag 2 prior to extraction of the biological fluid.

The collecting bag 3 and the bag 2 containing the solution have for example a similar structure including an external envelope formed by two sheets of plastics material connected together, for example by welding, at their periphery so as to define an internal volume intended to receive the content. The sheets are formed from weldable and sterilisable flexible biocompatible plastics material, for example polyvinyl chloride.

The external envelope of each of the bags 2, 3 is provided with at least one orifice 4, 5, 6 arranged so as to allow the supply of the internal volume and/or the distribution of the content of the bag 2, 3.

The removal component 1 is associated at one end 7 of a first flexible tube 8, the other end 9 of which is in fluid communication with the collecting bag 3. This design enables the collecting bag 3 to be supplied in closed circuit with extracted fluid.

The bag 2 containing the additive anticoagulant and/or preservation solution is associated, by way of an outlet orifice 4, with one end 10 of a second flexible tube 11, the other end 12 of which is in fluid communication with the collecting bag 3. This design enables the collecting bag 3 to be supplied in closed circuit with anticoagulant and/or preservation solution.

The tubes 8, 11 are for example formed from dividable and weldable sterilisable biocompatible flexible plastics material, for example polyvinyl chloride.

An extraction device according to the invention also includes a peristaltic pump 13 able to partially constrict respectively the first 8 and the second 11 tube in a constriction area 14.

The peristaltic pump 13 used is of a conventional type, namely including a motor 15 actuating a shaft 16 on which there are mounted one or more cylindrical rotors 17, 18 and carrying rollers 19. In this type of pump 13, each rotor 17, 18 is able to constrict a flexible tube disposed on the running path of the rollers 19. The succession of compression and relaxation thus produced on the flexible tube causes the fluid to circulate inside the tube. The structure of this type of pump is well known to persons skilled in the art and will not be described any further in this description.

According to one embodiment of the invention, the rate of constriction of the first 8 and second 11 tubes is substantially identical. In a specific embodiment, this characteristic is implemented using a single rotor 17 for constricting the two tubes 8, 11. In another specific embodiment, the two rotors 17, 18 are designed to constrict respectively the two tubes 8, 11 at an identical tangential speed when the shaft 16 rotates. In a variant, these two rotors 17, 18 are identical. These two specific embodiments are described in more detail below.

According to an exemplary embodiment of the invention, the ratio between the cross-section of the second tube 11 through which the additive solution passes and that of the first tube 8 through which the extracted fluid passes is substantially equal to the proportion in volume of additive anticoagulant and/or preservation solution to be added to the extracted biological fluid.

When the pump 13 is actuated, the rollers 19 constrict each tube 8, 11 with a substantially identical tangential speed so that the flow rate within each tube 8, 11 is proportional to the cross-section through which the fluid passes. This is because the flow rate inside a tube is the product of the speed of flow of the fluid, that is to say here the tangential speed of constriction of the tube, and the cross-section of the tube through which the fluid passes.

According to an embodiment of the invention, the collecting bag 3 is supplied with the extracted biological fluid and with the additive anticoagulant and/or preservation solution in the desired volume proportions.

First, second and third specific embodiments of an extraction device are described below, in which the first 8 and second 11 tubes are arranged so as to allow the mixing of the anticoagulant and/or preservation solution with the extracted fluid downstream of the constriction area. Thus the anticoagulant and/or preservation solution is never directed towards the patient, which prevents any accidental injection of this solution into the patient or donor.

Figure 2:
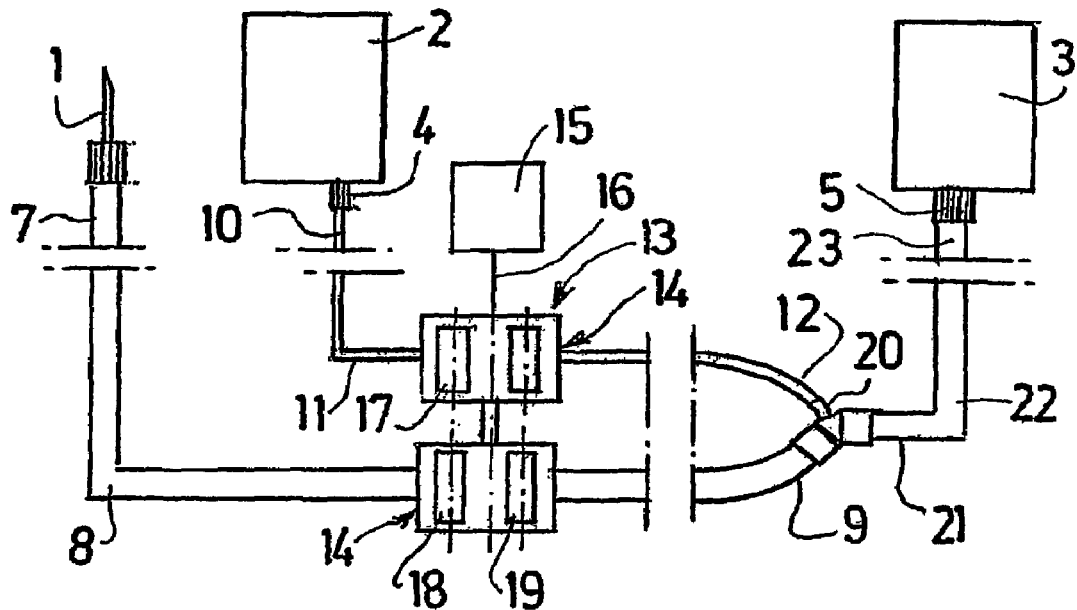
FIG. 2 depicts schematically, in elevation and flat views, a second variant of a first embodiment of an extraction device of the present invention in which a junction is provided downstream of the constriction area so as to supply the collecting bag through a single tube.

In the first specific embodiment of the extraction device, depicted in FIGS. 1 and 2, the peristaltic pump 13 includes two identical cylindrical rotors 17, 18. The rotors 17, 18 each carry rollers 19 able to constrict respectively the first 8 and the second 11 tubes.

In a first variant of this first specific embodiment depicted in FIG. 1, the first 8 and second 11 tubes are associated with the collecting bag 3 respectively by way of inlet orifices 5, 6.

In a second variant of this first specific embodiment depicted in FIG. 2, a junction 20, for example a Y junction, is provided downstream of the constriction area 7 so as to connect the first 8 and second 11 tubes to a first end 21 of a tube 22. The second end 23 of the tube 22 is connected to an input port 5 of the collecting bag 3. The cross-section of the tube 22 must be sufficient to prevent any overpressure in the device, but is not fixed at a precise value. In this variant the collecting bag 3 is supplied with extracted biological fluid and with anticoagulant and/or preservation solution by way of the tube 22.

Figure 3:
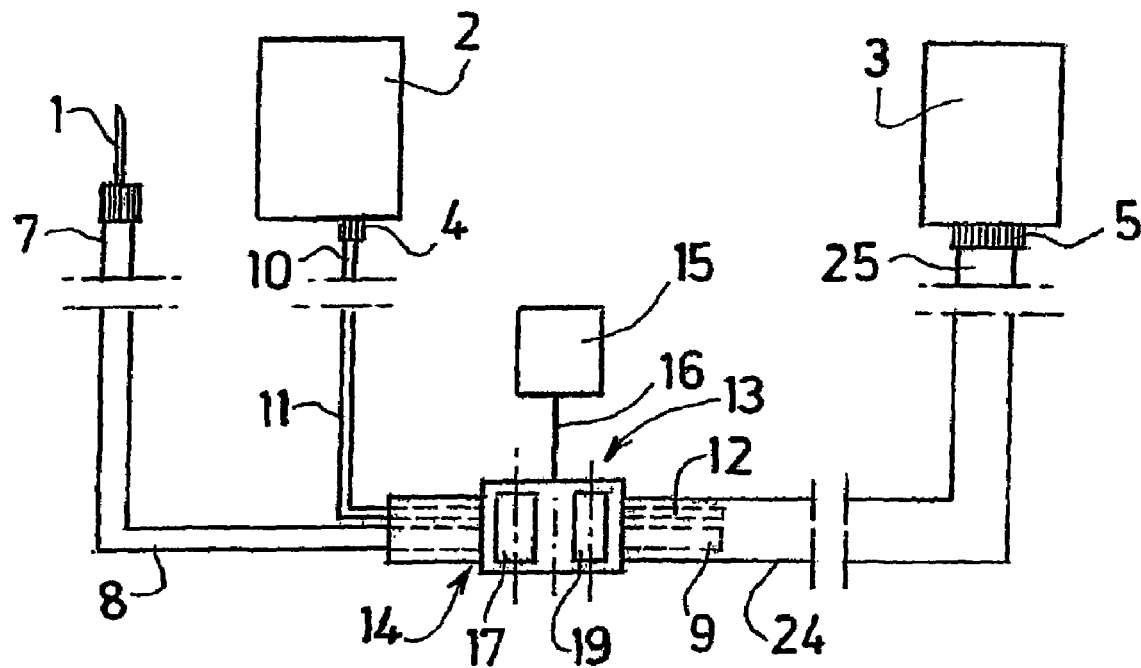
FIG. 3 depicts schematically, in elevation and flat views, a second embodiment of an extraction device of the present invention in which the collecting bag is supplied by a single tube in which the first and second tubes are associated, the tubes being constricted by the same rotor.

In a second specific embodiment of the extraction device, depicted in FIG. 3, the first 8 and second 11 tubes are associated in a sealed fashion in a tube 24, the downstream end 25 of which is connected to an input port 5 of the collecting bag 3. In the depicted embodiment the tubes 8, 11, 24 form a parallel double aperture assembly. This association is effected upstream of the constriction area 14 of the peristaltic pump 13, which comprises a single cylindrical rotor 17 carrying rollers 19 able to constrict the tubes 8, 11, 24.

In a variant of the second specific embodiment, the first 8 and second 11 tubes end downstream of the constriction area 14. The extracted fluid and the anticoagulant and/or preservation solution are then transported by the tube 24 from the downstream end 9, 12 of the first 8 and second 11 tubes to the collecting bag 3.

Figure 4:
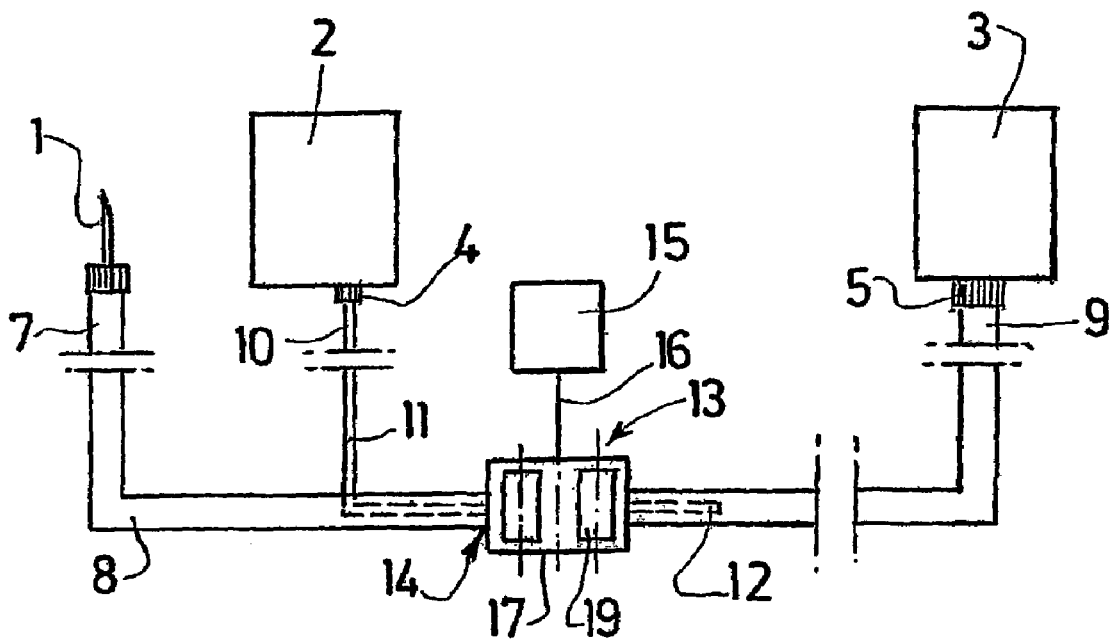
FIG. 4 depicts schematically, in elevation and flat views, a third embodiment of an extraction device of the present invention in which the collecting bag is supplied by the first tube in which the second tube is disposed, the tubes being constricted by the same rotor.

In a third specific embodiment of the extraction device, depicted in FIG. 4, the second tube 11 is introduced in a sealed fashion inside the first tube 8 so as to form an assembly of the concentric double aperture type. The downstream end 9 of the first tube 8 is then connected to an input port 5 of the collecting bag 3. In this embodiment, the cross-section of the first tube 8 through which the extracted fluid passes is equal to the cross-section of the first tube 8 minus that of the second tube 11.

The introduction of the second tube inside the first tube is effected upstream of the constriction area 14 formed by the peristaltic pump 13, which comprises a single cylindrical rotor 17 carrying rollers 19 able to constrict the first 8 and second 11 tubes.

In a variant of the third specific embodiment, the second tube 11 is closed downstream of the constriction area 14. The extracted fluid and the anticoagulant and/or preservation solution are then transported by the first tube 8 from the downstream end 12 of the second tube 11 to the collecting bag 3.

According to various embodiments of the invention, the collecting bag 3 can be incorporated, by way of an outlet orifice, in a more complex system, which includes for example other bags, tubes, clamps or filters. Such a solution can make it possible, after the collection of the whole blood and possibly dissociation of the removal component 1 and of the bag 2 by cutting and welding the corresponding tubes 8, 11, 22, 24, to effect in closed circuit the filtration and separation of the whole blood into its various constituents.

In a particular example, the device is intended to effect in closed circuit the extraction of the whole blood of a donor and the addition of an anticoagulant solution of the CPD type.

According to the standard in force in France, after addition, the volume proportion of additive CPD solution of to whole blood should be 14%. According to an embodiment of the invention in compliance with this standard, the ratio between the cross-section of the second tube 11 through which the solution passes and that of the first tube 8 through which the fluid passes is then fixed at 0.14. For example, the cross-section of the first tube 8 may be 0.7 cm$^2$ while that of the second tube 11 is 0.1 cm$^2$.

In an additional embodiment of the invention, the peristaltic pump 13 is able to constrict the first 8 and second 11 tubes simultaneously. Such an embodiment makes it possible to supply the collecting bag 3 with the extracted fluid and with the anticoagulant and/or preservation solution simultaneously so as to improve the mixing by stirring in the collecting bag 3.

The invention therefore makes it possible to effect the closed-circuit extraction of a biological fluid and the addition of an anticoagulant and/or preservation solution in a collecting bag 3 whilst having, at any time, a volume proportion of added solution in the extracted fluid which is fixed at the desired value. Thus, whatever the quantity of biological fluid collected, the content of the collecting bag 3 is at a desired proportion so that it can be used for medical and other purposes.

Although only exemplary embodiments of the invention are specifically described above, it will be appreciated that modifications and variations of the invention are possible without departing from the spirit and intended scope of the invention.

We claim:

1. A device for extracting a biological fluid, comprising:
    a) a first flexible tube including a constriction area and a pre-determined cross-section, the first flexible tube operable to transport a biological fluid;
    b) a second flexible tube including a constriction area and a pre-determined cross section, the second flexible tube operable to transport an additive solution;
    c) a collecting bag operable to receive the biological fluid transported by the first flexible tube and the additive solution transported by the second flexible tube, such that the biological fluid and the additive solution are deposited therein;
    d) at least one peristaltic pump, which is coupled to the first flexible tube and the second flexible tube, and is operable to partially constrict the first flexible tube and to partially constrict the second flexible tube at a substantially uniform rate,
    wherein the second flexible tube is introduced inside the first flexible tube in a sealed fashion upstream of the constriction area of the first flexible tube;
    wherein the second flexible tube ends downstream of the constriction area of the first flexible tube, such that the additive solution exits the second flexible tube downstream of the constriction area and is transported by the first flexible tube, and the biological fluid and additive solution are deposited in the collecting bag by way of the first flexible tube;
    wherein the additive solution and the biological fluid are deposited in the collecting bag in volumes proportionally determined by the ratio between the pre-determined cross-sections of the first flexible tube and the second flexible tube; and
    wherein the additive solution is substantially restricted from passing upstream of the constriction area of the first flexible tube.

2. The device of claim 1 further comprising a removal component for the removal of the biological fluid from a source operably connected to the first flexible tube.

3. The device of claim 1 further comprising an additive bag in which additive solution is located operably connected to the second flexible tube.

4. The device of claim 1 wherein the biological fluid is blood and the additive solution comprises an anticoagulant or preservation solution.

5. The device of claim 2 wherein the anticoagulant or preservation solution comprises CPD.

6. The device of claim 1 wherein the peristaltic pump is operable to constrict the first and second flexible tubes simultaneously.

7. The device of claim 1, wherein the additive solution and biological fluid are deposited in the collecting bag substantially simultaneously.

8. The device of claim 1, wherein the ratio between the cross-sections of the second flexible tube and the first flexible tube is between approximately 0.05 and 0.5.

9. The device of claim 1, wherein the ratio between the cross-sections of the second flexible tube and the first flexible tube is approximately 0.14.

10. The device of claim 1 wherein the introduction of the second flexible tube inside the first flexible tube in a sealed fashion upstream of the constriction area of the first flexible tube forms a concentric double aperture assembly.

11. A device for extracting a biological fluid, comprising:
    a) a first flexible tube including a constriction area and a pre-determined cross-section, the first flexible tube operable to transport a biological fluid;
    b) a second flexible tube including a constriction area and a pre-determined cross section, the second flexible tube operable to transport an additive solution;
    c) a collecting bag operable to receive the biological fluid transported by the first flexible tube and the additive solution transported by the second flexible tube, such that the biological fluid and the additive solution are deposited therein;
    d) at least one peristaltic pump, which is coupled to the first flexible tube and the second flexible tube; and
    wherein the second flexible tube is introduced inside the first flexible tube in a sealed fashion upstream of the constriction area of the first flexible tube;
    wherein the peristaltic pump comprises a cylindrical rotor that carriers rollers, and the rotor is operable to partially constrict the first flexible tube and to partially constrict the second flexible tube, which is inside the first flexible tube, at a substantially uniform rate,
    wherein the second flexible tube ends downstream of the constriction area of the first flexible tube, such that the additive solution exits the second flexible tube downstream of the constriction area and is transported by the first flexible tube, and the biological fluid and additive solution are deposited in the collecting bag by way of the first flexible tube;
    wherein the additive solution and the biological fluid are deposited in the collecting bag in volumes proportionally determined by the ratio between the pre-determined cross-sections of the first flexible tube and the second flexible tube; and
    wherein the additive solution is substantially restricted from passing upstream of the constriction area of the first flexible tube.

12. The device of claim 11 further comprising a removal component for the removal of the biological fluid from a source operably connected to the first flexible tube.

13. The device of claim 11 further comprising an additive bag in which additive solution is located operably connected to the second flexible tube.

14. The device of claim 11 wherein the biological fluid is blood and the additive solution comprises an anticoagulant or preservation solution.

15. The device of claim 13 wherein the anticoagulant or preservation solution comprises CPD.

16. The device of claim 11 wherein the peristaltic pump is operable to constrict the first and second flexible tubes simultaneously.

17. The device of claim 11, wherein the additive solution and biological fluid are deposited in the collecting bag substantially simultaneously.

18. The device of claim 11, wherein the ratio between the cross-sections of the second flexible tube and the first flexible tube is between approximately 0.05 and 0.5.

19. The device of claim 11, wherein the ratio between the cross-sections of the second flexible tube and the first flexible tube is approximately 0.14.

20. The device of claim 11 wherein the introduction of the first second flexible tube inside the first flexible tube in a sealed fashion upstream of the constriction area of the first flexible tube forms a concentric double aperture assembly.

\* \* \* \* \*